United States Patent
Murase et al.

(10) Patent No.: US 8,841,262 B2
(45) Date of Patent: Sep. 23, 2014

(54) AGENT FOR INHIBITING PERITONEAL MEMBRANE THICKENING

(75) Inventors: Hironobu Murase, Seki (JP); Tadashi Tomo, Oita (JP)

(73) Assignee: CCI Corporation, Gifu (JP)

( * ) Notice: Subject to any disclaimer, the term of this patent is extended or adjusted under 35 U.S.C. 154(b) by 139 days.

(21) Appl. No.: 13/259,558

(22) PCT Filed: Mar. 30, 2010

(86) PCT No.: PCT/JP2010/055728
§ 371 (c)(1),
(2), (4) Date: Dec. 13, 2011

(87) PCT Pub. No.: WO2010/113960
PCT Pub. Date: Oct. 7, 2010

(65) Prior Publication Data
US 2012/0083461 A1 Apr. 5, 2012

(30) Foreign Application Priority Data
Mar. 31, 2009 (JP) .................................. 2009-085557

(51) Int. Cl.
*A61K 31/7048* (2006.01)
*C07H 15/26* (2006.01)
*A61K 9/00* (2006.01)
*A61M 1/28* (2006.01)

(52) U.S. Cl.
CPC ............ *A61K 31/7048* (2013.01); *A61M 1/28* (2013.01); *C07H 15/26* (2013.01); *A61K 9/0019* (2013.01)
USPC .......................................................... 514/26

(58) Field of Classification Search
None
See application file for complete search history.

(56) References Cited

FOREIGN PATENT DOCUMENTS

| EP | 0804931 A2 * | 9/1987 | ............ A61K 45/06 |
|---|---|---|---|
| EP | 0611152 | 8/1994 | |
| EP | 0611152 A1 | 8/1994 | |
| EP | 0742012 A2 | 11/1996 | |
| EP | 0965344 | 12/1999 | |
| EP | 0965344 A1 | 12/1999 | |
| JP | 8-301-784 | 11/1996 | |
| JP | A-1996301784 | 11/1996 | |
| JP | A-2001031588 | 6/2001 | |
| JP | 2001-181191 | 7/2001 | |
| JP | 2001-31588 | 2/2011 | |
| WO | 01/02004 | 1/2001 | |

OTHER PUBLICATIONS

Sudhir Kapoor, Tulsi MUKHERJEe, Tsutomu V. Kagiya, Cherupally Krishnan K. Nair. Redox Reactions of Tocopherol Monoglucoside in Aqueous Solutions: a Pulse Radiolysis Study. J. Radiat. Res., 43, 99-106 (2002).*

Dobbie, J. W. (1992). Pathogenesis of peritoneal fibrosing syndromes (sclerosing peritonitis) in peritoneal dialysis. Peritoneal Dialysis International, 12(1), 14-27.*

Chung, et al., "Optimal Use of Peritoneal Dialysis in Patients with Diabetes," Peritoneal Dialysis International, vol. 29 (2009), Supplement 2.

Murase, et al., "Antioxidant Activity of a Novel Vitamin E Derivative 2-(α-D-Glucopyranosyl) Methyl-2,5,7,8-Tetramethylchroman-6-OL," Free Radical Biology & Medicine, vol. 24, No. 2, pp. 217-225, 1998.

Riesenhuber, et al., "Quercetin Protects Human Mesothelial Cells Against Exposure to Peritoneal Dialysis Fluid," Pediatric Nephrology (2007) 22:1205-1208.

Bozkurt, et al: "Can N-Acetylcysteine Preserve Peritoneal Function and Morphology in Encapsulating Peritoneal Sclerosis?" Peritoneal Dialysis International, vol. 29, 2008.

Noh, et al: "Oxidative stress during peritoneal dialysis: Implications in functional and structural changes in the membrane", International Society of Nephrology, 2006.

Noh, H. et al, Oxidative stress during peritoneal dialysis: Implications in functional and structural changes in the membrane, Kidney International, 2006, vol. 69, No. 11, p. 2022-2028 Abstract; p. 206, left column, line 49 to right column, line 18.

Bozkurt, D. et al, Can N-acetylcysteine preserve peritoneal function and morphology in encapsulating peritoneal sclerosis?, Peritoneal Dialysis International, Feb. 2009, vol. 29, No. Suppl. 2, p. S202-S205, Abstract; p. 203, left column, lines 12 to 16, lines 35 to 38.

Lee, H.B. et al, Mechanisms of epithelial-mesenchymal transition of peritoneal mesothelial cells during peritoneal dialysis, Journal of Korean Medical Science, 2007, vol. 22, No. 6, p. 943-945, Abstract.

(Continued)

*Primary Examiner* — Shaojia Anna Jiang
*Assistant Examiner* — Dale R Miller
(74) *Attorney, Agent, or Firm* — Cesari and McKenna, LLP

(57) ABSTRACT

The present invention is directed to an agent for inhibiting peritoneal membrane thickening which enables inhibition/prevention or treatment of the peritoneal membrane thickening and which mitigates adverse effect, and a dialysis fluid comprising the aforementioned thickening inhibitory agent.

The above-described problem is solved by administration of an agent for inhibiting peritoneal membrane thickening, comprising as an effective ingredient a chromanol glycoside represented by the following chemical formula (i), wherein the structural variables are described herein:

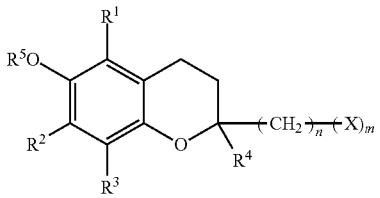

Chemical Formula 1)

2 Claims, 5 Drawing Sheets

(56) References Cited

OTHER PUBLICATIONS

Maragoudakis, E. Michael et al. "Inhibition of Basement Membrane Biosynthesis Prevents Angiogenesis" The Journal of Pharmacology. Volume 244 : 729, Feb. 1988.

Ingber, D.E. et al. "A Possible Mechanism for Inhibition of Angiogenesis by Angiostatic Steroids: Induction of Capillary Basement Membrane Dissolution." Endocrinology, 119: 1768, 1986.

Yoshio et al. "TNP-470, an angiogenesis inhibitor, suppresses the progression of peritoneal fibrosis in mouse experimental model", 2004.

Mishima et al. "Enhanced expression of heat shock protein 47 in rat model of peritoneal fibrosis." Peritoneal dialysis international, vol. 23, No. 1, Jan. 2003.

Okada et al., "Selective depletion of fibroblasts preserves morphology and the functional integrity of peritoneum in transgenic mice with peritoneal fibrosing syndrome" Kidney International, vol. 64, 1722-1732, 2003.

* cited by examiner ary 2003.

AGENT FOR INHIBITING PERITONEAL MEMBRANE THICKENING

CROSS REFERENCE TO RELATED APPLICATIONS

This application is a National Stage of International Application No. PCT/JP2010/055728, filed on Mar. 30, 2010, which claims priority to Japanese Application No. 2009-085557, filed Mar. 31, 2009. The contents of the prior applications are incorporated herein by reference in their entirety.

TECHNICAL FIELD

The present invention relates to an agent for inhibiting peritoneal membrane thickening which inhibits thickening of the peritoneal membrane.

BACKGROUND ART

It is said that patients who are receiving dialysis treatment for renal failure caused by deterioration or loss of kidney function are now about 220,000 in Japan, and about 95% of the aforementioned patients are receiving hemodialysis treatment using an extracorporeal blood circulation system, and remaining 5% of the patients are receiving peritoneal dialysis. In the case of medical treatment by hemodialysis, generally, the patient needs to remove waste products from exteriorized blood about 3 times a week spending almost 4 hours for 1 cure in the specialty hospital, and therefore, time constraints to the patient is strong. On the other hand, in the peritoneal dialysis, a catheter is embedded in the abdomen of the patient in advance, and a hypertonic dialysis fluid is introduced and stored through the aforementioned catheter in the inside of the abdominal cavity surrounded by the peritoneal membrane which covers internal organs such as the stomach and the intestine; this generates a difference in osmotic pressure between the stored dialysis fluid and the body fluid, and through the use of this osmotic pressure difference, excess water and waste products in the body are transferred to the peritoneal dialysis fluid in the abdominal cavity from the peritoneal capillary vessel. Therefore, since the medical treatment by peritoneal dialysis does not require a device for blood exteriorization as compared with hemodialysis, the burden on patients is low from the viewpoint of the "quality of life".

However, the patient who is receiving peritoneal dialysis treatment may develop encapsulating peritoneal sclerosis (EPS), peritoneal sclerosis, or peritoneal fibrosis and the like which are known as a general term of disorder of peritoneal membrane thickening. Cause of the peritoneal membrane thickening has not been clarified to date, however, for example, on the basis of assumption that neoangiogenesis may be involved in the peritoneal membrane thickening from the fact that abnormalities of blood vessel and increased number of blood vessel are observed in the thickened peritoneal tissue, and that vascular endothelial growth factor (VEGF) is present in high concentration in the intra-abdominal fluid of patients who is receiving peritoneal dialysis treatment, a study on the inhibition of peritoneal membrane thickening by administrating TNP-470 that is an agent for inhibiting vascular endothelial growth factor (VEGF) which is a growth factor having an action to facilitate neoangiogenesis has been reported in Non-Patent Literature 1. According to this study, by the administration of TNP-470, inhibition of neoangiogenesis and suppression of myofibroblastic cell proliferation have been reported.

In addition, in Non-Patent Literature 2, it has been reported to the effect that the expression of molecular chaperon Hsp47 specific for collagen is a cause of the peritoneal membrane thickening, and type I and type III collagen are produced when the Hsp47 is expressed in mesothelial cell and actin-positive cell. Furthermore, as an invention for inhibiting the peritoneal membrane thickening in relation to this report, there is Patent Literature 1. Patent Literature 1 describes that after the peritoneal membrane thickening is produced in rat by inoculating chlorhexidine gluconate in the abdominal cavity in advance, an oligonucleotide is administered as a substance of inhibiting Hsp47 in the abdominal cavity.

In addition, as a technology focused on the relationship between the above-described abnormal production of collagen and neoangiogenesis, for example, an invention on suppressing production of collagen as shown in Patent Literature 2 is included. In the invention of the aforementioned Patent Literature 2, in addition to inhibiting the peritoneal membrane thickening by administration of a medical drug which inhibits vascular endothelial growth factor (VEGF) by the reason that neoangiogenesis maybe involved in the peritoneal membrane thickening as shown in the above-described Non-Patent Literature 1, based on the report describing that the collagen synthesis in extracellular skeleton such as basal membrane plays an important role in neoangiogenesis (Maragoudakis, E., Sarmonika, M., and Panoutsacopoulous, M., J. Pharmacol. Exp. Ther., 244:729, 1988; Ingber, D. E., Madri, J. A., and Folkman, J., Endocrinology, 199:1768, 1986), it was confirmed that a glycoprotein complex derived from Basidiomycete belonging to Trametes versicolor inhibited specifically the synthesis of Hsp47 in the tissue cell of pathological condition. According to this invention, it has been described to the effect that the glycoprotein complex inhibits not only fibrosis and hardening of organ and tissue, but the above-described metastasis of cancer can also be suppressed since it has been clarified that the stroma which is constituted by type I collagen and fibronectin as a basic skeleton plays a role of guide in leading a released cancer cell to invasion into adjacent vascular channel in cancer metastasis.

Furthermore, in Non-Patent Literature 3, it has been reported that the chlorhexidine-induced peritoneal lesion is remitted by administration of ganciclovir which is an antiviral drug, describing to the effect that after the peritoneal membrane thickening is produced in mouse by administrating chlorhexidine in the abdominal cavity previousely, and the peritoneal membrane thickening is alleviated when the ganciclovir is infused into the abdominal cavity in 2 weeks.

PRIOR ART LITERATURES

Patent Literatures

Patent Literature 1: JP A2001-31588
Patent Literature 2: JP A8-301784

Non-Patent Literatures

Non-Patent Literature 1: TNP-470, an neoangiogenesis inhibitor, suppresses the progression of peritoneal fibrosis in mouse experimental model, Yoshio et al., Kidney International, vol. 64, 1722-1732, 2003.

Non-Patent Literature 2: Enhanced expression of heat shock protein 47 in rat model of peritoneal fibrosis, Mishima et al., Peritoneal Dialysis International, vol. 23, No. 1, January 2003.

Non-Patent Literature 3: Selective depletion of fibroblasts preserves morphology and the functional integrity of peritoneum in transgenic mice with peritoneal fibrosing syndrome, Okada et al., Kidney International, vol. 66, 1677-1685, 2004

SUMMARY OF INVENTION

Problem to be Solved by the Invention

However, in the prior works, a variety of approaches have been practiced to suppress the peritoneal membrane thickening because the cause of peritoneal membrane thickening has been left unexplained, and although the difference of effectiveness in contrast with the present invention cannot be verified simply, for example, in the Non-Patent Literature 3, as much as 50 mg/kg of ganciclovir is administered. In the case of a normal subject having normal kidney function, dosage of ganciclovir is instructed to medicate with 5 mg/kg in every 12 hours; therefore, in the study of Non-Patent Literature 3, dosage is 10 times greater than that (5 mg/kg) for the subject with normal kidney function. Furthermore, since the dosage of ganciclovir for the patient with renal failure (dialysis patients) is generally provided to be 5 mg/kg, once every 48 hours to 96 hours, it can be understood that the dosage is obviously excessive dose. Furthermore, since ganciclovir has adverse effects such as neutropenia and thrombocytopenia, it may have restrictions in use. In addition, in Non-Patent Literature 2, 20 mg/kg of TNP-470 is administered as well, and wariness of side effects remains.

In addition, in Patent Literature 1 and Patent Literature 2, predefined oligonucleotide and glycoprotein are used as a main component, therefore, handling of these substances is not simple; and further, in Patent Literature 2, on the occasion of generating new blood vessel by migration of endothelial cell to the extracellular skeleton and proliferation in the angiogenesis, production of type I collagen which is a main component of the aforementioned extracellular skeleton can be inhibited, however, no result on suppression and inhibition of thickening of the peritoneal membrane has been disclosed.

Consequently, the purpose of the present invention is to provide a thickening inhibitory agent for inhibiting peritoneal membrane thickening which enables inhibition, prevention or treatment of the peritoneal membrane thickening and which mitigates adverse effect, and a dialysis fluid comprising the aforementioned thickening inhibitory agent.

Means for Solving the Problem

The above-described purpose of the present invention is accomplished by an agent for inhibiting peritoneal membrane thickening comprising a chromanol glycoside shown in the following chemical formula (1):

[Chemical Formula 1]

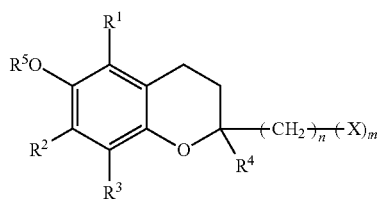

(Chemical Formula 1)

(in this regard, however, $R^1$, $R^2$, $R^3$, and $R^4$ each represent a hydrogen atom or a lower alkyl group which may be the same as or different from each other; $R^5$ represents a hydrogen atom, a lower alkyl group or a lower acyl group; X represents a mono-sugar residue or an oligo-sugar residue in which a hydrogen atom of a hydroxyl group in sugar residue may be substituted by a lower alkyl group or a lower acyl group; n is an integer of 0 to 6; and m is an integer of 1 to 6), or by dialysis fluid having the aforementioned agent for inhibiting peritoneal membrane thickening.

Effect of the Invention

According to the present invention, adverse effects can be reduced, and inhibition/prevention or treatment of the peritoneal membrane thickening is made possible. Moreover, since the agent for inhibiting peritoneal membrane thickening relevant to the present invention or the aforementioned agent for inhibiting peritoneal membrane thickening comprises chromanol glycoside as an active ingredient, these can exert a property of amphiphilic molecule showing a very high water solubility (about 100 g/100 mL) and an oil solubility (distribution coefficient in octanol/water system>3) which are a property of the aforementioned chromanol glycoside. Accordingly, the agent for inhibiting peritoneal membrane thickening comprising chromanol glycoside of the present invention or the aforementioned agent for inhibiting peritoneal membrane thickening can permeate cell membrane and further it can enter also in the cell, because handling thereof is simple and easy, and in contrast to the conventional water insoluble or poorly-soluble agents, a high lipophilic property is retained even after dissolving in water.

BRIEF DESCRIPTION OF THE DRAWINGS

[FIG. 1-B]
FIG. 1-B shows the peritoneal membrane of TMG group which was stained with H.E;
[FIG. 1-C]
FIG. 1-C shows the peritoneal membrane of control group which was stained with H.E;
[FIG. 2-B]
FIG. 2-B shows the peritoneal membrane of TMG group in which type I collagen was stained;
[FIG. 2-C]
FIG. 2-C shows the peritoneal membrane of control group in which type I collagen was stained;
[FIG. 3-B]
FIG. 3-B shows the peritoneal membrane of TMG group in which Hsp47 positive cells were stained;
[FIG. 3-C]
FIG. 3-C shows the peritoneal membrane of control group in which Hsp47 positive cells were stained.

EMBODIMENTS FOR CARRYING OUT THE INVENTION

Figure 1A:
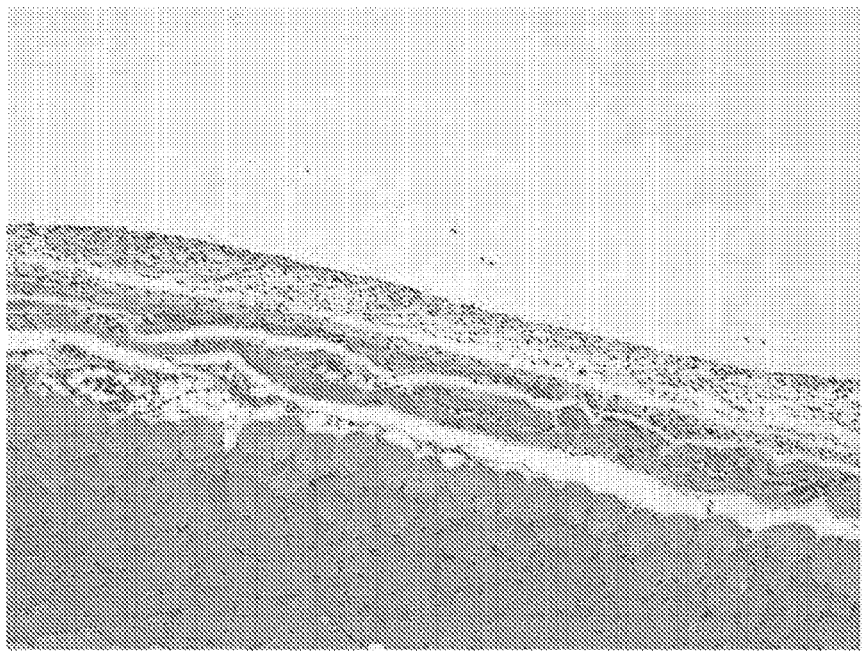
[FIG. 1-A]
FIG. 1-A shows the peritoneal membrane of CG group which was stained with H.E.

It should be noted that the present application is based on the Japanese Patent Application No. 2009-85557, filed on Mar. 31, 2009, and the disclosure has been incorporated herein in entirety by reference.

The first aspect of the present invention is a thickening inhibitory agent comprising a chromanol glycoside shown in the following chemical formula (1):

[Chemical Formula 2]

(Chemical Formula 1)

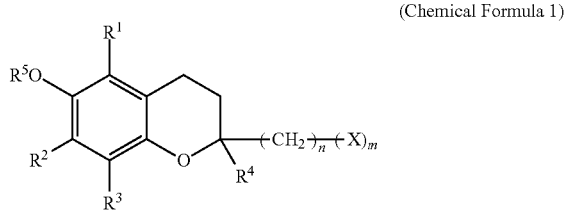

(in this regard, however, $R^1$, $R^2$, $R^3$, and $R^4$ each represent a hydrogen atom or a lower alkyl group which may be the same as or different from each other; $R^5$ represents a hydrogen atom, a lower alkyl group or a lower acyl group; X represents a mono-sugar residue or an oligo-sugar residue in which a hydrogen atom of a hydroxyl group in sugar residue may be substituted by a lower alkyl group or a lower acyl group; n is an integer of 0 to 6; and m is an integer of 1 to 6).

Thereby, inhibition/prevention or treatment of the peritoneal membrane thickening can be made possible; and the usable time period of about ten years due to deterioration in peritoneal function which is one of the problems in the conventional peritoneal dialysis can be extended.

For example, according to JP-A-2001-066306, from the knowledge that a main component of the thickened peritoneal membrane at the pathogenic state of peritoneal membrane thickening is collagen fiber, it has been confirmed that if the concentration of a substance which acts on the collagen as represented by fibronectin is measured, state of pathogenesis and state of progress of the peritoneal membrane thickening can be figured out more correctly, and the peritoneal membrane thickening can be diagnosed with high accuracy. Since the probability of involvement of abnormally increased collagen as a cause of peritoneal membrane thickening is high from this fact, it is conceivable that the peritoneal membrane thickening can be inhibited by inhibiting and suppressing production of a substance such as collagen which forms extracellular skeleton. And so, as shown in the aforementioned Patent Literature 1 and Non-Patent Literature 2, etc., since Hsp47 is considered to act as a specific molecular chaperone of collagen in the stage of processing of the procollagen within endoplasmic reticulum, triple-helix formation, or transportation and secretion of procollagen from endoplasmic reticulum to Golgi apparatus in the cell, enhanced expression of Hsp47 stimulates accumulation of collagen molecule in the extracellular skeleton. And so, in Examples mentioned later, effect of the thickening inhibitory agent relevant to the present invention has been determined by measuring the proportion of type I collagen occupied in the parietal peritoneum and Hsp47 positive cell. As a result, as shown in Examples mentioned later, production of type I collagen and/or Hsp47 positive cell can be suppressed or inhibited by the thickening inhibitory agent relevant to the present invention.

In the above-described chemical formula (1) of the chromanol glycoside relevant to the present invention, the lower alkyl group of $R^1$, $R^2$, $R^3$, $R^4$ and $R^5$ may have 1 to 8 carbon atoms, and preferably 1 to 6 carbon atoms, and includes, for example, methyl group, ethyl group, propyl group, isopropyl group, butyl group, isobutyl group, pentyl group, isopentyl group, hexyl group, heptyl group, octyl group, and the like. Among them, methyl group and ethyl group are preferable. In addition, the lower acyl group of $R^5$ may have 1 to 8 carbon atoms, and preferably 1 to 6 carbon atoms, and includes, for example, formyl group, acetyl group, propionyl group, butyryl group, isobutyryl group, valeryl group, isovaleryl group, pivaloyl group, hexanoyl group, heptanoyl group, octanoyl, and the like. Among them, an acetyl group, a propionyl group and a butyryl group are preferable. Also, the mono-saccharide residue of X includes sugar residue such as a glucose, galactose, fucose, xylose, mannose, rhamnose, fructose, arabinose, lyxose, ribose, allose, altrose, idose, talose, deoxyribose, 2-deoxyribose, quinovose, abequose, and the like. The oligo-sugar residue of X includes the ones in which 2 to 4 units of the above-described mono-sugars are bonded together, for example, sugar residue such as maltose, lactose, cellobiose, raffinose, xylobiose, sucrose, and the like. Among them, the mono-sugar residue such as glucose, galactose, fucose, xylose, rhamnose, mannose, fructose, and the like are preferable. Also, a hydrogen atom of hydroxyl group in the sugar residue of X may be substituted by a lower alkyl group, and preferably a lower alkyl group having 1 to 8 carbon atoms, or a lower acyl group, and preferably a lower acyl group having 1 to 10 carbon atoms. Further, n is an integer of 0 to 6, and preferably 1 to 4, and m is an integer of 1 to 6, and preferably 1 to 3.

The chromanol glycoside represented by the chemical formula (1) relevant to the present invention is not particularly limited, as long as it is a compound represented by the above-described chemical formula (1), and specifically, the chromanol glycoside includes 2-(($\alpha$ or $\beta$)-D-glucopyranosyl)methyl-2,5,7,8-tetramethylchroman-6-ol; 2-(($\alpha$ or $\beta$)-D-glucopyranosyl)ethyl-2,5,7,8-tetramethylchroman-6-ol; 2-(($\alpha$ or $\beta$)-D-glucopyranosyl)propyl-2,5,7,8-tetramethylchroman-6-ol; 2-(($\alpha$ or $\beta$)-D-glucopyranosyl)isopropyl-2,5,7,8-tetramethylchroman-6-ol; 2-(($\alpha$ or $\beta$)-D-glucopyranosyl)butyl-2,5,7,8-tetramethylchroman-6-ol; 2-(($\alpha$ or $\beta$)-D-glucopyranosyl)isobutyl-2,5,7,8-tetramethylchroman-6-ol; 2-(($\alpha$ or $\beta$)-D-glucopyranosyl)pentyl-2,5,7,8-tetramethylchroman-6-ol; 2-(($\alpha$ or $\beta$)-D-glucopyranosyl)isopentyl-2,5,7,8-tetramethylchroman-6-ol; 2-(($\alpha$ or $\beta$)-D-glucopyranosyl)hexyl-2,5,7,8-tetramethylchroman-6-ol; 2-(($\alpha$ or $\beta$)-D-glucopyranosyl)heptyl-2,5,7,8-tetramethylchroman-6-ol; 2-(($\alpha$ or $\beta$)-D-glucopyranosyl)octyl-2,5,7,8-tetramethylchroman-6-ol; 2-(($\alpha$ or $\beta$)-D-galactopyranosyl)methyl-2,5,7,8-tetramethylchroman-6-ol; 2-(($\alpha$ or $\beta$)-D-galactopyranosyl)ethyl-2,5,7,8-tetramethylchroman-6-ol; 2-(($\alpha$ or $\beta$)-D-galactopyranosyl)propyl-2,5,7,8-tetramethylchroman-6-ol; 2-(($\alpha$ or $\beta$)-D-galactopyranosyl)isopropyl-2,5,7,8-tetramethylchroman-an-6-ol; 2-(($\alpha$ or $\beta$)-D-galactopyranosyl)butyl-2,5,7,8-tetramethylchroman-6-ol; 2-(($\alpha$ or $\beta$)-D-galactopyranosyl)isobutyl-2,5,7,8-tetramethylchroman-n-6-ol; 2-(($\alpha$ or $\beta$)-D-galactopyranosyl)pentyl-2,5,7,8-tetramethylchroman-6-ol; 2-(($\alpha$ or $\beta$)-D-galactopyranosyl)isopentyl-2,5,7,8-tetramethylchroman-an-6-ol; 2-(($\alpha$ or $\beta$)-D-galactopyranosyl)hexyl-2,5,7,8-tetramethylchroman-6-ol; 2-(($\alpha$ or $\beta$)-D-galactopyranosyl)heptyl-2,5,7,8-tetramethylchroman-6-ol; 2-(($\alpha$ or $\beta$)-D-galactopyranosyl)octyl-2,5,7,8-tetramethylchroman-6-ol; 2-(($\alpha$ or $\beta$)-L-fucopyranosyl)methyl-2,5,7,8-tetramethylchroman-6-ol; 2-(($\alpha$ or $\beta$)-L-fucopyranosyl)ethyl-2,5,7,8-tetramethylchroman-6-ol; 2-((($\alpha$ or $\beta$)-L-fucopyranosyl)propyl-2,5,7,8-tetramethylchroman-6-ol; 2-(($\alpha$ or $\beta$)-L-fucopyranosyl)isopropyl-2,5,7,8-tetramethylchroman-6-ol; 2-(($\alpha$ or $\beta$)-L-fucopyranosyl)butyl-2,5,7,8-tetramethylchroman-6-ol; 2-(($\alpha$ or $\beta$)-L-fucopyranosyl)isobutyl-2,5,7,8-tetramethylchroman-6-ol; 2-(($\alpha$ or $\beta$)-L-fucopyranosyl)pentyl-2,5,7,8-tetramethylchroman-6-ol; 2-(($\alpha$ or $\beta$)-L-fucopyranosyl)isopentyl-2,5,7,8-tetramethylchroman-6-ol; 2-(($\alpha$ or $\beta$)-L-fucopyranosyl)hexyl-2,5,7,8- tetramethylchroman-6-ol; 2-((α or β)-L-fucopyranosyl)heptyl-2,5,7,8-tetramethylchroman-6-ol; 2-((α or β)-L-fucopyranosyl)octyl-2,5,7,8-tetramethylchroman-6-ol; 2-((α or β)-D-xylopyranosyl)methyl-2,5,7,8-tetramethylchroman-6-ol; 2-((α or β)-D-xylopyranosyl)ethyl-2,5,7,8-tetramethylchroman-6-ol; 2-((α or β)-D-xylopyranosyl)propyl-2,5,7,8-tetramethylchroman-6-ol; 2-((α or β)-D-xylopyranosyl)isopropyl-2,5,7,8-tetramethylchroman-6-ol; 2-((α or β)-D-xylopyranosyl)butyl-2,5,7,8-tetramethylchroman-6-ol; 2-((α or β)-D-xylopyranosyl)isobutyl-2,5,7,8-tetramethylchroman-6ol; 2-((α or β)-D-xylopyranosyl)pentyl-2,5,7,8-tetramethylchroman-6-ol; 2-((α or β)-D-xylopyranosyl)isopentyl-2,5,7,8-tetramethylchroman-6-ol; 2-((α or β)-D-xylopyranosyl)hexyl-2,5,7,8-tetramethylchroman6-ol; 2-((α or β)-D-xylopyranosyl)heptyl-2,5,7,8-tetramethylchroman-6-ol; 2-((α or β)-D-xylopyranosyl)octyl-2,5,7,8-tetramethylchroman-6-ol; 2-((α or β)-L-rhamnopyranosyl)methyl-2,5,7,8-tetramethylchroman-6-ol; 2-((α or β)-L-rhamnopyranosyl)ethyl-2,5,7,8-tetramethylchroman-6-ol; 2-((α or β)-L-rhamnopyranosyl)propyl-2,5,7,8-tetramethylchroman-6-ol; 2-((α or β)-L-rhamnopyranosyl)isopropyl-2,5,7,8-tetramethylchroman-n-6-ol; 2-((α or β)-L-rhamnopyranosyl)butyl-2,5,7,8-tetramethylchroman-6-ol; 2-((α or β)-L-rhamnopyranosyl)isobutyl-2,5,7,8-tetramethylchroman-6-ol; 2-((α or β)-L-rhamnopyranosyl)pentyl-2,5,7,8-tetramethylchroman-6-ol; 2-((α or β)-L-rhamnopyranosyl)isopentyl-2,5,7,8-tetramethylchroman-6-ol; 2-((α or β)-L-rhamnopyranosyl)hexyl-2,5,7,8-tetramethylchroman-6-ol; 2-((α or β)-L-rhamnopyranosyl)heptyl-2,5,7,8-tetramethylchroman-6-ol; 2-((α or β)-L-rhamnopyranosyl)octyl-2,5,7,8-tetramethylchroman-6-ol; 2-((α or β)-D-mannopyranosyl)methyl-2,5,7,8-tetramethylchroman6-ol; 2-((α or β)-D-mannopyranosyl)ethyl-2,5,7,8-tetramethylchroman6-ol; 2-((α or β)-D-mannopyranosyl)propyl-2,5,7,8-tetramethylchroman-6-ol; 2-((α or β)-D-mannopyranosyl)isopropyl-2,5,7,8-tetramethylchroman-6-ol; 2-((α or β)-D-mannopyranosyl)butyl-2,5,7,8-tetramethylchroman-6-ol; 2-((α or β)-D-mannopyranosyl)isobutyl-2,5,7,8-tetramethylchroman-6-ol; 2-((α or β)-D-mannopyranosyl)pentyl-2,5,7,8-tetramethylchroman-6-ol; 2-((α or β)-D-mannopyranosyl)isopentyl-2,5,7,8-tetramethylchroman-6-ol; 2-((α or β)-D-mannopyranosyl)hexyl-2,5,7,8-tetramethylchroman-6-ol; 2-((α or β)-D-mannopyranosyl)heptyl-2,5,7,8-tetramethylchroman-6-ol; 2-((α or β)-D-mannopyranosyl)octyl-2,5,7,8-tetramethylchroman-6-ol; 2-((α or β)-D-fructofuranosyl)methyl-2,5,7,8-tetramethylchroman-6-ol; 2-((α or β)-D-fructofuranosyl)ethyl-2,5,7,8-tetramethylchroman-6-ol; 2-((α or β)-D-fructofuranosyl)propyl-2,5,7,8-tetramethylchroman-6-ol; 2-((α or β)-D-fructofuranosyl)isopropyl-2,5,7,8-tetramethylchroman-6-ol; 2-((α or β)-D-fructofuranosyl)butyl-2,5,7,8-tetramethylchroman-6-ol; 2-((α or β)-D-fructofuranosyl)isobutyl-2,5,7,8-tetramethylchroman-6-ol; 2-((α or β)-D-fructofuranosyl)pentyl-2,5,7,8-tetramethylchroman-6-ol; 2-((α or β)-D-fructofuranosyl)isopentyl-2,5,7,8-tetramethylchroman-6-ol; 2-((α or β)-D-fructofuranosyl)hexyl-2,5,7,8-tetramethylchroman-6-ol; 2-((α or β)-D-fructofuranosyl)heptyl-2,5,7,8-tetramethylchroman-6-ol; and 2-((α or β)-D-fructofuranosyl)octyl-2,5,7,8-tetramethylchroman-6-ol.

The chromanol glycoside relevant to the present invention is not particularly limited, and may be synthesized by a known method, or a commercially available product may be purchased. For example, when the chromanol glycoside relevant to the present invention is synthesized by the method described in JP-A-07-118287, the glycoside can be produced by the enzyme reaction, comprising reacting 2-substituted alcohol represented by the following chemical formula (2):

[Chemical Formula 3]

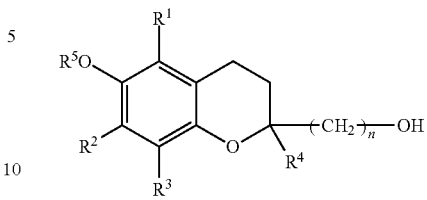

(Chemical Formula 2)

(in this regard, however, $R^1$, $R^2$, $R^3$, R4, R5 and n in the formula have the same meanings as above) and oligo-saccharides, soluble starch, starch, or cyclodextrin in the presence of an enzyme catalyzing a corresponding sugar transfer action, and bonding a specific hydroxyl group of the sugar specifically to the hydroxyl group at 2-position of the 2-substituted alcohol (enzyme method).

The 2-substituted alcohol represented by the chemical formula (2) to be used as a raw material in the above-described reaction (hereinafter, simply referred to as "2-substituted alcohol") is a known material, and can be obtained, for example, by the method disclosed in JP-B-01-43755, JP-B-01-49135, or the like. Also, for example, in the case of 2-substituted alcohol where $R^1$, $R^2$, $R^3$ and $R^4$ are each a methyl group, $R^5$ is a hydrogen atom, and n is 1, the 2-substituted alcohol can be obtained easily by heating trolox in diethyl ether under reflux in the presence of lithium aluminum hydride, and the like.

Moreover, as for an enzyme which catalyzes transglycosylation reaction employed in the above-described reaction, it is desirable to use properly as follows depending on the type of sugar to be used for the aforementioned reaction.

(1) In the case where a glucose residue is bound to 2-substituted alcohol by α-linkage:

(a) For maltooligosaccharide including any one from maltose roughly to maltotetraose, it is desirable to be processed by α-glucosidase (EC3.2.1.20). As to α-glucosidase, the one derived from almost all origins can be utilized, and specifically, α-glucosidase derived from *Saccharomyces* sp. (produced by TOYOBO Co., Ltd.), α-glucosidase derived from *Saccharomyces cerevisiae* (produced by Oriental Yeast Co., Ltd.), α-glucosidase derived from *Aspergillus niger* (produced by Amano Enzyme Inc.), α-glucosidase derived from *Saccharomyces* sp. (produced by Wako Pure Chemical Industries, Ltd.), α-glucosidase derived from Baker's yeast and α-glucosidase derived from *Bacillus* sp. (produced by SIGMA Aldrich Corp.) are included.

(b) For soluble starch or starch, it is desirable to be processed by 4-α-D-glucanotransferase (EC2.4.1.25).

(2) In the case where a glucose residue or maltooligosaccharide residue is bound to 2-substituted alcohol by α-linkage:

For maltooligosaccharide, soluble starch, starch, or cyclodextrin (α, β, γ) or the like, it is desirable to be processed by cyclodextrin glucanotransferase (EC2.4.1.19). A representative example includes cyclodextrin glucanotransferase derived from *Bacillus macerans* (produced by Amano Enzyme Inc.), cyclodextrin glucanotransferase derived from *Bacillus stearothermophilus* (produced by Hayashibara Biochemical Laboratories, Inc.), and as for the rest, cyclodextrin glucanotransferase derived from *Baccillus megaterium*, and cyclodextrin glucanotransferase derived from *Bacillus circulans* ATCC 9995, and so on.

(3) In the case where a glucose residue is bound to 2-substituted alcohol by β-linkage:
  (a) For oligosaccharide which consists of β-linkage such as cellobiose, curdlan or laminaran, it is desirable to be processed by β-glucosidase (EC3.2.1.21).
  (b) For cellobiose in the presence of phosphate, it is desirable to be processed by cellobiose phosphorylase (EC2.4.1.20).
(4) In the case where a galactose residue is bound to 2-substituted alcohol by α-linkage:
  (a) For melibiose, or raffinose or the like, it is desirable to be processed by α-galactosidase (EC3.2.1.22).
(5) In the case where a galactose residue is bound to 2-substituted alcohol by β-linkage:
  (a) For lactose or the like, it is desirable to be processed by β-galactosidase (EC3.2.1.23).
  (b) For arabinogalactan or the like, it is desirable to be processed by endo-1, 4-β-galactanase (EC3.2.1.89).
(6) In the case where a fructose residue is bound to 2-substituted alcohol by β-linkage:
  (a) For sucrose, raffinose, melibiose or the like, it is desirable to be processed by levansucrase (EC2.4.1.10).
  (b) For sucrose, it is desirable to be processed by β-fructofuranosidase (EC3.2.1.26).
  (c) For inulin or the like, it is desirable to be processed by inulin fructotransferase (EC2.4.1.93).
(7) In the case where a mannose residue is bound to 2-substituted alcohol by α-linkage:
  (a) For methyl mannopyranoside or the like, it is desirable to be processed by α-mannosidase (EC3.2.1.24), for example, by α-mannosidase derived from jack beans (produced by SIGMA Aldrich Corp.).

The reaction conditions in the above-described reaction may vary depending on the type of chromanol glycoside and enzyme to be used, however, for example, when the chromanol glycoside in which m in the chemical formula (1) is 1 is synthesized using α-glucosidase, it is desirable to dissolve the 2-substituted alcohol in sugar solution. To this end, it is desirable to add an organic solvent including, for example, dimethyl sulfoxide, N, N-dimethylformamide, methanol, ethanol, acetone, acetonitrile, and the like, and in view of increasing transferase activity of α-glucosidase, dimethyl sulfoxide and N, N-dimethylformamide are used preferably. Concentration of organic solvent to be added is 1 (v/v) % to 50 (v/v) %, however in consideration of reaction efficiency, it is preferable to be 5 (v/v) % to 35 (v/v) %.

As for concentration of 2-substituted alcohol, it is desirable to be a saturated concentration or a nearly-saturated concentration in the reaction solution. Type of sugar may be the one of low molecular weight within the range from maltose to maltotetraose, and maltose is preferable. The concentration of the sugar is 1 (w/v) % to 70 (w/v) %, preferably it is 30 (w/v) % to 60 (w/v) %. pH is 4.5 to 7.5, preferably 5.0 to 6.5. Reaction temperature is 10° C. to 70° C., preferably 30° C. to 60° C. Reaction time is 2 hours to 24 hours preferably 1 hour to 40 hours. In this regard, however, it goes without saying that these conditions may be influenced by the quantity of enzyme, and the like to be used. After completion of the reaction, the objective chromanol glycoside is obtained in high purity by processing the reaction mixture with column chromatography using XAD (produced by Organo Corp.) as a carrier.

In addition, for example, as for the reaction conditions in the case where the chromanol glycoside whose m in the chemical formula (1) is 1 is synthesized using cyclodextringlucanotransferase, it is desirable to dissolve the 2-substituted alcohol in sugar solution. For this purpose, addition of an organic solvent is desirable, and the organic solvent includes dimethyl sulfoxide, N, N-dimethylformamide, methanol, ethanol, acetone, acetonitrile, and the like. Concentration of organic solvent to be added is 1 (v/v) % to 50 (v/v) %, however in consideration of reaction efficiency, it is desirable to be 5 (v/v) % to 35 (v/v) %. As for the concentration of 2-substituted alcohol, it is desirable to be saturated concentration or a high concentration near thereto in the reaction solution.

As to type of sugar to be used in the above-described reaction, maltooligosaccharides having polymerization degree greater than that of maltotriose, soluble starch, starch, cyclodextrin (α, β, γ), and the like are included preferably. Concentration of the sugar is 1 (w/v) % to 70 (w/v) %, preferably it is 5 (w/v) % to 50 (w/v) %. pH is 4.5 to 8.5, preferably 5.0 to 7.5. Reaction temperature is 10° C. to 70° C., preferably 30° C. to 60° C. Reaction time is 1 to 60 hours, preferably 2 to 50 hours. In this regard, however, these conditions are influenced by the quantity of enzyme to be employed. The chromanol glycoside produced by such reactions provides a mixture of those having the number of m from 1 to 8. And so, by processing this mixture using glucoamylase (EC3.2.1.3), only the chromanol glycoside whose m in the chemical formula (1) is 1 can be obtained. The reaction temperature in this occasion is 20° C. to 70° C., preferably 30° C. to 60° C., and the reaction time is 0.1 to 40 hours, preferably 1 to 24 hours. In this regard, however, these conditions are influenced by the quantity of enzyme to be employed. Subsequently, the solution after above-described processing with glucoamylase is treated with column chromatography using XAD (produced by Organo Corp.) as a carrier, and thereby, the chromanol glycoside whose m in the chemical formula (1) is 1 is obtained in high purity.

In the case where the chromanol glycoside whose m in the chemical formula (1) is 2 is obtained, under the same conditions as described above, a chromanol glycoside having a form of mixture whose m in the chemical formula (1) is 1 to 8 obtained by cyclodextringlucanotransferase is reacted with β-amylase (EC3.2.1.2), and thereby only the chromanol glycoside whose m in the chemical formula (1) is 1 or 2 is obtained. Reaction temperature in this case is 20° C. to 70° C., preferably 30° C. to 60° C., and reaction time is 0.1 to 40 hours, preferably 1 to 24 hours. In this regard, however, these conditions are influenced by the quantity of enzyme to be employed. By treating the solution after processing by β-amylase with column chromatography using XAD (produced by Organo Corp.) as a carrier, the chromanol glycoside whose m in the chemical formula (1) is 2 is obtained in high purity, as well as the chromanol glycoside whose m in the chemical formula (1) is 1 is also obtained at the same time.

In the case where the chromanol glycoside whose m in the chemical formula (1) is 3 or more is obtained, under the same conditions as described above, a chromanol glycoside having a form of mixture whose m in the chemical formula (1) is 1 to 8 obtained by cyclodextringlucanotransferase is treated by preparative chromatography and the like using HPLC, and thereby high purity chromanol glycoside can be obtained for respective numbers of m.

In the above-described embodiments, cases of binding a glucose residue or a malt oligosaccharide residue with the 2-substituted alcohol as a sugar residue were described, however, an case in which galactose residue, β-glucose residue, mannose residue, fructose residue or the like is bound to the 2-substituted alcohol as a sugar residue can also be used preferably in the present invention. In such cases, the objective chromanol glycoside can be obtained in high purity by performing the same operations as in the above-described embodiments except for using respective appropriate enzymes as explained in the clause of the enzyme which catalyzes the above-described transglycosylation action (JP-A-9-249688, JP-A-11-21291).

On the other hand, the chromanol glycoside used in the present invention can be produced according to the method described in JP-A-11-279192 by condensing the above-described 2-substituted alcohol whose hydroxyl group at position 6 is protected with a protecting group (hereafter, referred to as "sugar receptor") with a derivative of sugar in which a leaving group has been introduced into an anomeric position and the other hydroxyl group has been protected by a protecting group (hereafter, referred to as "sugar donor") (organic synthesis method).

The protective group for protecting the hydroxyl group located in 6-position of the sugar receptor to be used in the above-described reaction includes acetyl group, benzoyl group, pivaloyl group, chloroacetyl group, levulinoyl group, benzyl group, p-methoxybenzyl group, allyl group, t-butyldimethylsilyl group, t-butyldiphenylsilyl group, trimethylsilyl group, trityl group, and the like, particularly, acetyl group and benzoyl group are preferable.

The leaving group introduced into anomeric position of the sugar donor to be used in the above-described reaction includes halogen atom such as chlorine, bromine and fluorine; sulfur compound such as thiomethyl group, thioethyl group and thiophenyl group; trichloroacetimide group; and the like, particularly, bromine, chlorine, thiomethyl group, thioethyl group, thiophenyl group and trichloroacetimide group are preferable. In addition, the protective group for protecting the hydroxyl group in a position other than the anomeric position includes acyl type protective group such as acetyl group, benzoyl group, pivaloyl group, chloroacetyl group and levulinoyl group; and ether type protective group such as benzyl group, p-methoxybenzyl group, allyl group, t-butyldimethylsilyl group, t-butyldiphenylsilyl group, trimethylsilyl group and trityl group. Among them, acyl type protective group, in particular, acetyl group is preferable.

These sugar donors can be easily prepared by introducing a protective group to all of hydroxyl groups in a sugar by a known method, subsequently substituting the anomeric position by a leaving group.

The condensation reaction of the above-described sugar donor and the sugar accepter will be described. Firstly, a sugar donor and a sugar accepter are dissolved in a nonpolar solvent. Amounts of the sugar donor and the sugar accepter to be charged may be 1.0 to 1.5, and preferably 1.1 to 1.3 in molar ratio of the sugar donor to the sugar accepter. Nonpolar solvent includes methylene chloride, benzene, and the like.

Next, the condensation reaction of the sugar donor and the sugar accepter is carried out under anhydrous condition in the presence of an activating agent. The activating agent includes boron trifluoride/etherate complex, silver perchlorate, silver trifluoromethanesulfonate, mercury bromide, mercury cyanide, N-iodosuccinimide-trifluoromethane sulfonic acid, dimethylmethylthiosulfonium triflate, p-toluenesulfonic acid, and the like. Particularly, when bromine is used as a leaving group of sugar derivative, it is preferable to use heavy metal salt such as silver perchlorate. Reaction temperature may be 5 to 30° C., and preferably 10 to 25° C., and reaction time is 12 to 48 hours, and preferably 20 to 30 hours.

Subsequently, by purifying the obtained reaction product with silica-gel column chromatography or the like, and deprotecting the protective group with sodium hydroxide, methanolic hydrochloric acid, or the like, the following compounds can be obtained:

2-(β-L-fucopyranosyl)methyl-2,5,7,8-tetramethylchroman-6-ol,
2-(α-L-rhamnopyranosyl)methyl-2,5,7,8-tetramethylchroman-6-ol,
2-(β-D-xylopyranosyl)methyl-2,5,7,8-tetramethylchroman-6-ol, and the like (JP-A-11-279192).

Since the thus obtained chromanol glycoside has generally a property of high water solubility and also rich in oil solubility, it can localize near the cell membrane, and can penetrate cell membrane, and further can also enter into the cell.

The agent for inhibiting peritoneal membrane thickening relevant to the present invention may contain the chromanol glycoside shown in the above-described chemical formula (1) alone as an active ingredient or may also contain another ingredient together. The aforementioned another ingredient includes pharmaceutically necessary substance, and additives such as pharmaceutically acceptable carrier, buffering agent, preservative, antioxidant, flavoring agent, coloring agent, and sweetener can also be employed appropriately. The aforementioned pharmaceutically acceptable carrier includes excipient such as lactose, dextrin, sucrose, mannitol and cornstarch, sorbitol, and auxiliary agent such as crystalline cellulose and polyvinyl pyrrolidone, and these substances can be used alone or in an appropriate combination. In addition, content of these excipient, auxiliary agent, or additives can be determined suitably by those skilled in the art. Alternatively, this preparation may contain other medicinal ingredients which do not inhibit the activity to inhibit the peritoneal membrane thickening.

The agent for inhibiting peritoneal membrane thickening of the present invention can be used as various types of pharmaceutical composition which comprises an active ingredient of the compound shown in the chemical formula (1) in combination with physiologically harmless solid or liquid formulation carrier. This pharmaceutical composition is formulated in various types of dosage form and used corresponding to dosing regimens. The dosage form includes tablet, granules, pellet, capsule, liquid preparation, syrup, suspension, emulsion, or injectable solution. As for the formulation carrier, commonly used excipient, binding agent, disintegrating agent, lubricant, coating agent, solubilizing agent, emulsifier, suspending agent, stabilizer or solvent can be used.

In addition, the compound shown in the chemical formula (1) relevant to the present invention and the above-described pharmaceutical composition can be used by oral administration, parenteral administration such as intravenous infusion, sustained-release medication by sustained-release formulation, and topical administration by a catheter for local administration and the like.

Furthermore, actual given dose of the compound shown in the chemical formula (1) relevant to the present invention depends on patient's age, severity of symptom, administration route, and the like, and generally accepted effective one-day dose for adult subject is, for example, 10 to 1000 mg, and preferably 20 to 600 mg. It is preferable to medicate with such dose by dividing into once to 5 times per day to a patient who needs such treatment.

The peritoneal dialysis fluid which inhibits the peritoneal membrane thickening relevant to the present invention preferably comprises chromanol glycoside shown in the above-described formula (1) and an osmotic pressure regulating agent.

Thereby, adverse effects are reduced and inhibition/prevention or medical treatment of peritoneal membrane thickening can be enabled.

At present, one of the causes of the peritoneal membrane thickening disease is also considered that the mesothelial cell on the surface of the peritoneum may produce a substance which forms extracellular skeleton such as collagen in response to an external stimulus, something like acidic dialysis fluid and advanced glycation end product, and which may cause fibroblast cell growth and thickening of collagen layer of the peritoneal membrane. However, as described above, the cause of the peritoneal membrane thickening has not yet been clarified. The peritoneal membrane thickening is inhibited by adding the chromanol glycoside relevant to the present invention to the dialysis fluid as shown in Example described later. Although actually it is still unknown by what mechanism the peritoneal membrane thickening is inhibited, it is conceivable that it may decrease external stimulus such as acidic dialysis fluid and advanced glycation end product of sugar such as glucose, or inhibiting collagen production and the growth of fibroblast cell and the like.

The dialysis fluid relevant to the present invention contains chromanol glycoside shown in the above-described formula (1) preferably in the concentration of 0.001 to 0.3 g/L, more preferably in the concentration of 0.002 to 0.2 g/L, and further more preferably in the concentration of 0.005 to 0.15 g/L. When the concentration of the above-described chromanol glycoside is lower than 0.001 g/L, the effect is not expectable; and when it is higher than 0.3 g/L, the effect consistent with concentration is not expectable.

The osmotic pressure regulating substance relevant to the present invention is not particularly limited, so long as it is an osmotic pressure regulating substance which is safe for living organisms. The osmotic pressure regulating substance includes, for example, sugars, peptides, amino acids, and the like, however, sugars are preferable. The aforementioned sugars include monosaccharide such as glucose, galactose, mannose and fructose; disaccharide such as sucrose, maltose, lactose and trehalose; polysaccharide such as glycogen, maltoorigosaccharide, isomaltoorigosaccharide, oligoglycosyl-sucrose, fructooligosaccharide and galactooligosaccharide; sugar alcohol such as maltitol, erythritol and xylitol, and derivatives thereof. Among them, glucose and glucose derivative are preferable. Moreover, the aforementioned glucose derivative may be a chemically modified glucose, or may be a polysaccharide which is composed of glucose as a base unit. Further, more preferably it is D-glucose.

In addition, the osmotic pressure regulating substance relevant to the present invention also includes a dialysis fluid which comprises amino acid in place of glucose or together with glucose as. For example, a specified composition of amino acid mixture proposed in JP No. 3483885: a dialysis fluid comprising leucine, valine, threonine, isoleucine, lysine, histidine, methionine, phenylalanine, tryptophan, alanine, proline, arginine, glycine, serine, tyrosine, aspartate, and glutamate, in a concentration of 1.6 w/v % or less, wherein methionine is 48 mg or less per total 100 mL of solution; phenylalanine/tyrosine ratio is about 1.3 to about 3.0: and basic amino acid/acidic amino acid ratio is about 1 to about 2.2, can also be used.

The peritoneal dialysis fluid relevant to the present invention preferably comprises the above-described osmotic pressure regulating substance in a concentration of 2 to 35 g/L, more preferable in a concentration of 5 to 30 g/L, and further more preferably in a concentration of 10 to 25 g/L.

Osmotic pressure of the peritoneal dialysis fluid relevant to the present invention is preferably 300 to 500 mOsm/kg, and more preferably 330 to 490 mOsm/kg.

The above-described osmotic pressure regulating substance and osmotic pressure is preferably used within the above-described range depending on the excessive amount of patient's body fluid.

The peritoneal dialysis fluid relevant to the present invention may further comprise another component if need arises, for example, electrolytes (sodium ion, calcium ion, magnesium ion, chlorine ion, and the like) maybe contained. When the above-described electrolyte is added to the peritoneal dialysis fluid, the electrolyte is preferably added so that the concentration thereof falls into the range of the following composition example.

In addition, the peritoneal dialysis fluid relevant to the present invention may be acidic dialysis fluid or neutral dialysis fluid, and as for pH of the peritoneal dialysis fluid relevant to the present invention is preferably 4 to 8, and more preferably 4.5 to 7.5.

To maintain electroneutrality of the peritoneal dialysis fluid relevant to the present invention, an alkalizing agent such as lactate ion and bicarbonate ion can also be contained. Moreover, corresponding to the concentration difference between total cation and chlorine ion, for example, organic acid or the like can be contained. Such organic acid includes, for example, propionic acid, malic acid, fumaric acid, succinic acid, oxalacetic acid, N-acetylglycine, N-acetyl-L-cysteine, glutaric acids, glucuronic acids, ascorbic acid, citric acid, isocitric acid, gluconic acid, N-acetyl-L-aspartic acid, N-acetyl-L-glutamic acid, N-acetyl-L-methionine, N-acetyl-L-proline, N-acetyl-L-valine, N-acetyl-L-glutamine, N-acetyl-L-arginine, N-acetyl-L-histidine, N-acetyl-L-leucine, N-acetyl-L-tryptophan, salt thereof, and the like. When the above-described alkalizing agent and organic acid are added to the peritoneal dialysis fluid, preferably these substances are added so that concentrations thereof fall into the ranges of the following composition example.

Method for preparing the peritoneal dialysis fluid relevant to the present invention is not particularly limited, and it can be prepared in the same manner as in the case of the commonly used peritoneal dialysis fluid, for example, by dissolving cation such as sodium chloride, calcium chloride, magnesium chloride, sodium lactate, calcium salt, magnesium salt, and sodium bicarbonate, chlorine ion source and acid component in water. Moreover, after the peritoneal dialysis fluid prepared by dissolving each solute is packed in a soft plastic bag or glass container, it is desirable to carry out high pressure steam sterilization or hot water sterilization.

Example of the composition of the peritoneal dialysis fluid relevant to the present invention (in the case where a solvent is water):

Sodium ion ($Na^+$): 130 mEq/L to 135 mEq/L;
Calcium ion ($Ca^{2+}$): 2 mEq/L to 4 mEq/L;
Magnesium ion ($Mg^{2+}$): 0.4 mEq/L to 0.6 mEq/L;
Chlorine ion ($Cl^-$): 94 mEq/L to 97 mEq/L;
Glucose: 12 g/L to 40 g/L;
Chromanol: 0.01 g/L to 0.1 g/L; and
Alkalizing agent containing lactate ion: 35 mEq/L to 45 mEq/L.

EXAMPLES

Hereinafter, the present invention will be explained by referring to the following Examples and Comparative Examples. In this regard, however, the technical scope of the present invention is by no means limited only to the following Examples. In addition, in the following Examples, measurement of length of tissue, measurement of % area, and counting of cell number were carried out using image analysis software, Image J (reference literature: Yodosha Co., Ltd., Image Analysis Text; Lecture on Practicing NIH Image, Scion Image, and Image J, revised 3rd edition).

Example 1

<Preparation of Chlorhexidine-induced Peritoneal Membrane Thickening Model>

The peritoneal membrane thickening model was prepared by administrating chlorhexidine into the abdominal cavity of a mouse (C57/BL6, male, 7 week-old, 21+/−1 g of body weight) (Junor B J R, Briggs J D, Forwell M A, Dobbie J W, Henderson I: Sclerosing peritonitis The contribution of chlorhexidine in alcohol. Perit Dial Bull 101-104, 1985). Specifically, the mice were divided into CG group (five animals), control group (four animals), and TMG group (five animals), and each group received the following treatment (CG Group)

A solution of 0.1% chlorhexidine/15% ethanol/physiological saline (0.2 mL) was administered into the abdominal cavity of the mice 3 times a week.

(Control Group)

A solution of 15% ethanol/physiological saline (0.2 mL) was administered into the abdominal cavity of the mice 3 times a week.

(TMG Group)

A solution which was made by adding TMG (abbreviation of 2-(α-D-glucopyranosyl)methyl-2,5,7,8-tetramethylchroman-6-ol) to a solution of 0.1% chlorhexidine/15% ethanol/physiological saline to give a concentration of 15 mg/L (0.2 mL) was administered into the abdominal cavity of the mice 3 times a week. After carrying out the above-described treatment in each group, all the mice were subjected to necropsy in 22 days.

It should be noted that TMG is an abbreviation of 2-(α-D-glucopyranosyl)methyl-2,5,7,8-tetramethylchroman-6-ol, and is shown by the following chemical formula (3).

[Chemical Formula 4]

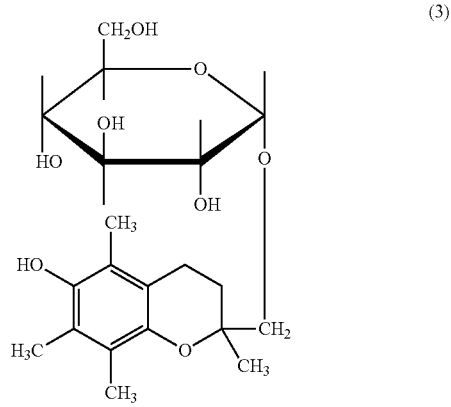

(3)

<Preparation of Peritoneal Tissue Sections>

After anesthetizing with ether, the mouse was brought into death by blood removal, and then the peritoneal membrane was collected from left lateroabdominal region. Collection of the peritoneal membrane was carried out so that the collection site became the same for each mouse. Next, after fixing the obtained peritoneal membrane with 10% formalin/0.1 M phosphate buffer (pH 7.2), the membrane was embedded in paraffin and tissue sections with 2 to 3 μm thickness were prepared. These sections were made perpendicularly to the peritoneal membrane so that thickness of the membrane could be measured.

Example 2

<Effect on the Peritoneal Membrane Thickening>

Figure 1B:
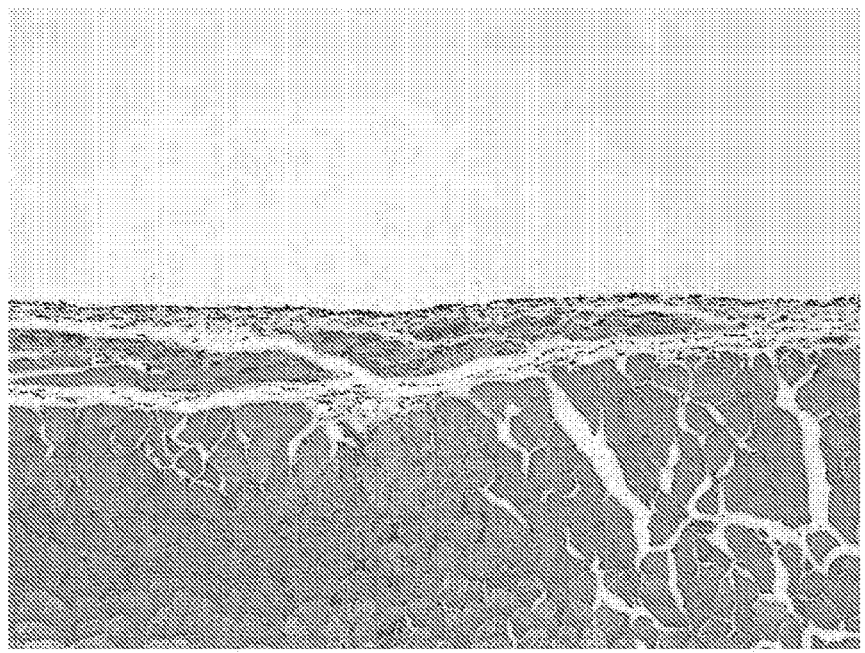
Figure 1C:
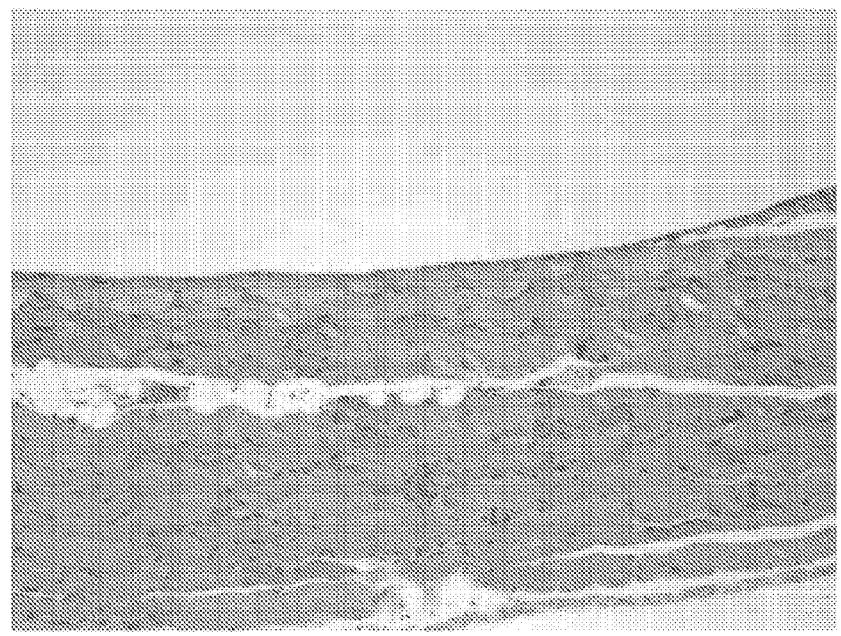

The results of H. E staining of the peritoneal tissue sections prepared in Example 1 are shown in FIG. 1-A, FIG. 1-B, and FIG. 1-C. Moreover, thickness of the peritoneal membrane was measured. Ten positions were measured at random for 1 animal, and a mean value thereof was calculated. The results were shown in the following Table 1.

TABLE 1

| | Thickness of peritoneal membrane thickening (μm) | |
|---|---|---|
| CG group | 82.3 ± 24.5 | Refer to FIG. 1-A |
| TMG group | 42.1 ± 19.7[a] | Refer to FIG. 1-B |
| Control group | 9.1 ± 2.8[b] | Refer to FIG. 1-C |

[a]$P < 0.0001$ versus CG;
[b]$P < 0.0001$ versus CG (t-test)

From the results of FIG. 1-A to FIG. 1-C and Table 1, it can be confirmed that the peritoneal membrane thickening caused by CG administration has been inhibited by administration of TMG.

Example 3

<Effect on Type I Collagen>

Figure 2A:
[FIG. 2-A]
FIG. 2-A shows the peritoneal membrane of CG group in which type I collagen was stained.
Figure 2B:
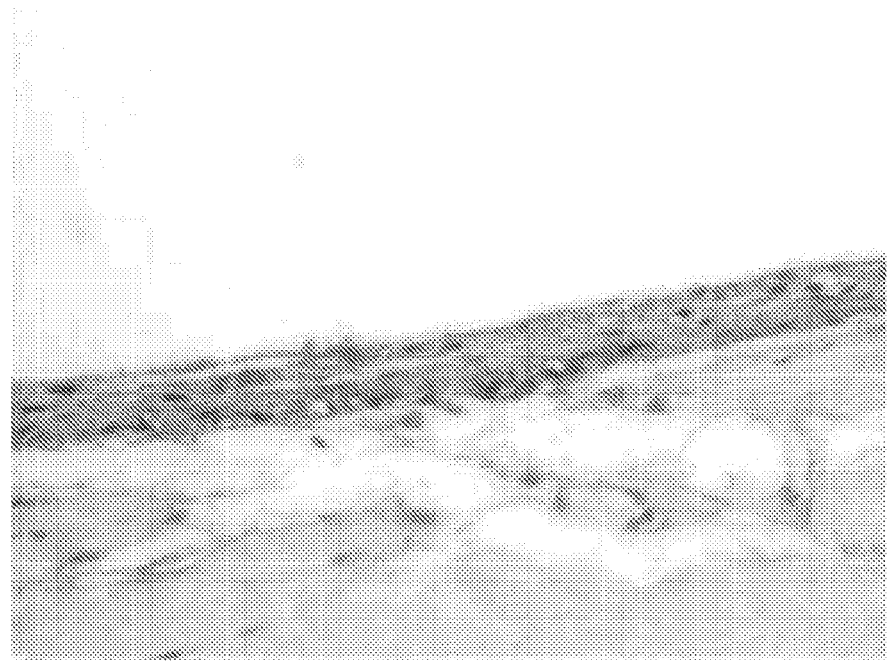
Figure 2C:
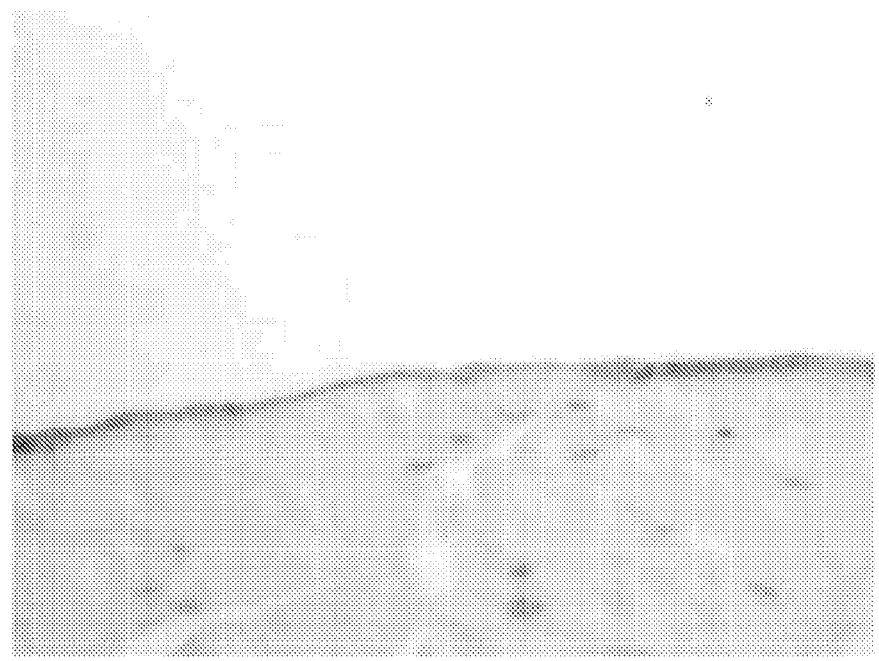

The results of immunostaining of the peritoneal tissue sections prepared in Example 1 by polyclonal antibody against type I collagen, RABBIT ANTI MOUSE COLLAGEN I (polyclonal IgG) (AbD Serotec; UK) are shown in FIG. 2-A, FIG. 2-B, and FIG. 2-C. Activation of the antibody was performed by autoclaving, and the antibody diluted 250 times was used for immunostaining. In a 400-fold magnification of visual field, ratio of an area occupied by type I collagen to the parietal peritoneum was measured at 10 positions at random for 1 animal, and a mean value thereof was calculated. The results are shown in the following Table 2.

TABLE 2

| | Type I collagen occupied area (%) | |
|---|---|---|
| CG group | 18.55 ± 2.06[a] | Refer to FIG. 2-A |
| TMG group | 8.68 ± 1.85[a] | Refer to FIG. 2-B |
| Control group | 1.94 ± 0.46[b] | Refer to FIG. 2-C |

[a]$P < 0.0001$ versus CG;
[b]$P < 0.0001$ versus CG (t-test)

From the results of FIG. 2-A to FIG. 2-C and Table 2, it can be confirmed that production of type I collagen caused by CG administration has been inhibited by administration of TMG.

Example 4

<Inhibitory Effect on Hsp47 Positive Cell>

Figure 3A:
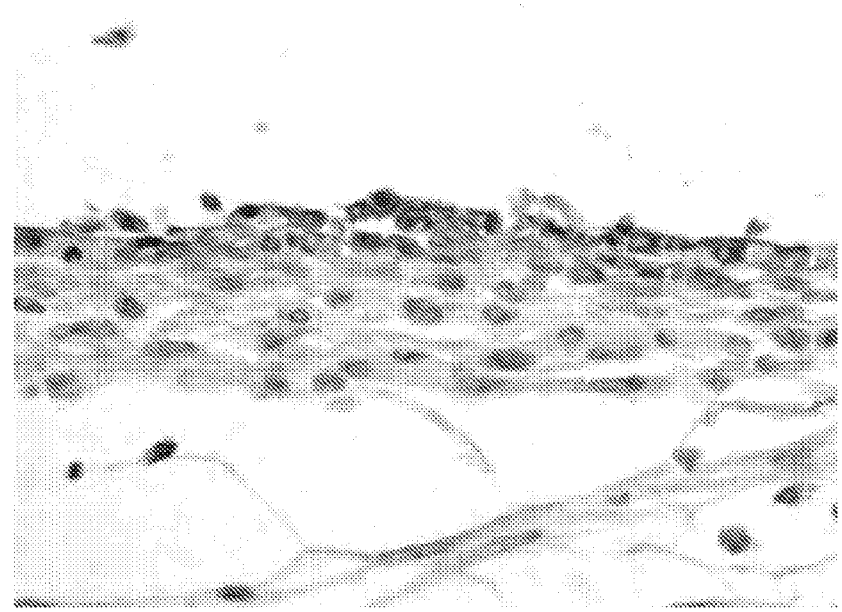
[FIG. 3-A]
FIG. 3-A shows the peritoneal membrane of CG group in which Hsp47 positive cells were stained.
Figure 3B:
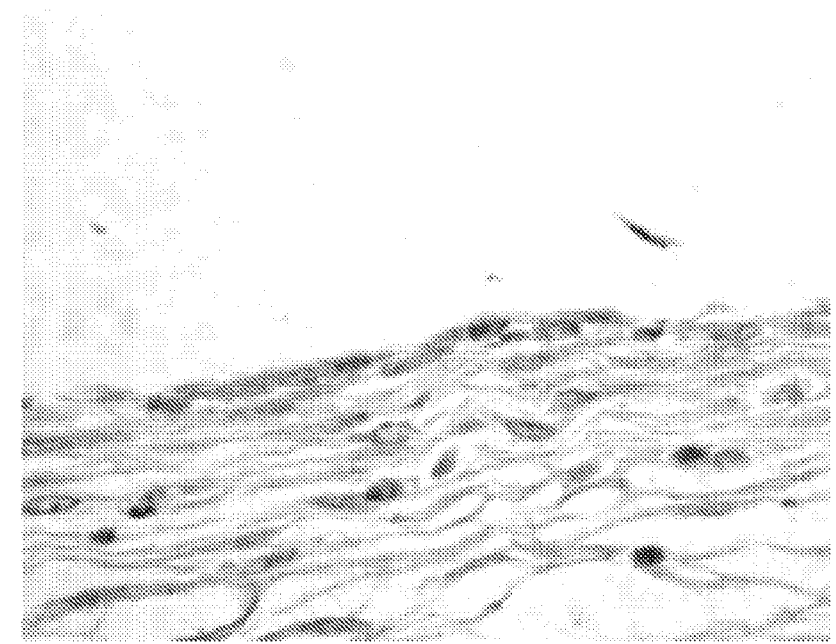
Figure 3C:

The results of immunostaining of the peritoneal tissue sections prepared in Example 1 by Hsp47 Polyclonal Antibody (BioVision, Inc.: USA) which is a polyclonal antibody against heat shock protein 47 (Hsp47) are shown in FIG. 3-A, FIG. 3-B, and FIG. 3-C. Activation of the antibody was performed by autoclaving, and the antibody diluted 20 times was used for immunostaining. In a 400-fold magnification of visual field, Hsp47 positive cell was measured at 10 positions at random for 1 animal, and a mean value thereof was calculated. The results are shown in the following Table 3.

TABLE 3

|  | Hsp47 positive cell (cell number) |  |
|---|---|---|
| CG group | 109.2 ± 22.3 | Refer to FIG. 3-A |
| TMG group | 49.0 ± 9.3[a] | Refer to FIG. 3-B |
| Control group | 25.0 ± 5.0[b] | Refer to FIG. 3-C |

[a] $P < 0.0001$ versus CG;
[b] $P < 0.0001$ versus CG (t-test)

From the results of FIG. 3-A to FIG. 3-C and Table 3, it can be confirmed that increase of Hsp47 positive cell caused by CG administration has been inhibited by administration of TMG.

What is claimed is:

1. A method for inhibiting peritoneal membrane thickening comprising administering to a subject in need thereof an agent comprising as an active ingredient, 2-(a-D-glucopyranosyl)methyl-2,5,7,8-tetramethylchroman-6-ol, wherein the active ingredient is dissolved in a solvent at a concentration of 0.005 to 0.015 g/L.

2. The method according to claim 1, wherein the agent is administered to a subject in need thereof in a peritoneal dialysis fluid that includes the agent and an osmotic pressure regulating agent.

* * * * *